(12) United States Patent
Ponce (10) Patent No.: US 8,105,307 B2
(45) Date of Patent: Jan. 31, 2012

(54) DETERMINING AN INJECTION REGION IN A HETEROGENEOUS BODY STRUCTURE

(75) Inventor: Maria Inmaculada Rodriguez Ponce, München (DE)

(73) Assignee: Brainlab AG, Feldkirchen (DE)

( * ) Notice: Subject to any disclaimer, the term of this patent is extended or adjusted under 35 U.S.C. 154(b) by 62 days.

(21) Appl. No.: 11/858,992

(22) Filed: Sep. 21, 2007

(65) Prior Publication Data
US 2008/0082048 A1    Apr. 3, 2008

Related U.S. Application Data

(60) Provisional application No. 60/829,403, filed on Oct. 13, 2006.

(30) Foreign Application Priority Data

Sep. 28, 2006   (EP) .................................... 06020436

(51) Int. Cl.
*A61M 31/00* (2006.01)

(52) U.S. Cl. ................. 604/500; 604/890.1; 604/891.1; 604/892.1; 600/300

(58) Field of Classification Search .................. 604/500, 604/890.1–892.1, 422
See application file for complete search history.

(56) References Cited

U.S. PATENT DOCUMENTS

| | | | | |
|---|---|---|---|---|
| 4,639,244 A | * | 1/1987 | Rizk et al. | 604/19 |
| 5,016,615 A | * | 5/1991 | Driller et al. | 601/2 |
| 5,720,720 A | * | 2/1998 | Laske et al. | 604/500 |
| 5,826,065 A | * | 10/1998 | Hinsberg et al. | 717/104 |
| 5,972,369 A | * | 10/1999 | Roorda et al. | 424/424 |
| 6,369,116 B1 | * | 4/2002 | Wong et al. | 514/171 |
| 6,549,803 B1 | * | 4/2003 | Raghavan et al. | 600/431 |
| 2003/0118649 A1 | * | 6/2003 | Gao et al. | 424/471 |
| 2007/0078338 A1 | * | 4/2007 | Pedain et al. | 600/431 |

FOREIGN PATENT DOCUMENTS

| | | |
|---|---|---|
| EP | 1 316 324 | 6/2003 |
| EP | 1 376 443 | 1/2004 |
| EP | 1376443 A1 * | 1/2004 |

(Continued)

OTHER PUBLICATIONS

Zhdanov et al. "Application of Percolation Theory tothe Analysis of Pore Structure by Capillary Condensation Measurements." React. Kinet. Catal. Lett., vol. 8, Issue 1: 185-180 (1986).*

(Continued)

*Primary Examiner* — Jackie Ho
*Assistant Examiner* — Scott Medway
(74) *Attorney, Agent, or Firm* — Renner, Otto, Boisselle & Sklar, LLP (57) ABSTRACT

A device and method for determining at least one infusion and/or injection region for infusing and/or injecting a medical drug into a heterogeneous body structure in order to achieve a distribution of the medical drug in a desired target region of the heterogeneous body structure is provided. The device and method provide at least one property of the heterogeneous body structure that influences the spatial distribution of the medical drug in the heterogeneous body structure; and determine the at least one infusion and/or injection region from which the medical drug is to be transported through the heterogeneous body structure to the at least one target region as a function of the at least one property of the heterogeneous body structure and a position of the desired target region.

20 Claims, 2 Drawing Sheets

FOREIGN PATENT DOCUMENTS

| | | |
|---|---|---|
| EP | 1 396 233 | 3/2004 |
| EP | 1396233 A1 * | 3/2004 |
| WO | 01/85230 | 11/2001 |
| WO | 2006/085288 | 8/2006 |

OTHER PUBLICATIONS

Netti et al. "Macro- and Microscopic Fluid Transport in Living Tissues: Application to Solid Tumors." AIChE Journal, vol. 43, No. 3: 818-834 (1997).*

Baish et al. "Role of Tumor Vascular Architecture in Nutrient and Drug Delivery: An Invasion Percolation-Based Network Model." Microvascular Research, Issue 51: 327-346 (1996).*

Kier et al. "A Cellular Automata Model of the Percolation Process." J. Chem. Inf. Comput. Sci. Issue 39: 326-332 (1999).*

Saltzman, Mark. "Drug Delivery: Engineering Principles for Drug Therapy." Oxford University Press. 2001. pp. 82-84.*

* cited by examiner

DETERMINING AN INJECTION REGION IN A HETEROGENEOUS BODY STRUCTURE

RELATED APPLICATION DATA

This application claims priority of U.S. Provisional Application No. 60/829,403 filed on Oct. 13, 2006, which is incorporated herein by reference in its entirety.

FIELD OF THE INVENTION

The present invention relates generally to infusion of a material into a body and, more particularly, to determining a suitable infusion and/or injection region for infusing and/or injecting a medical drug into a heterogeneous body structure.

BACKGROUND OF THE INVENTION

A heterogeneous body structure is a body structure that includes a plurality of different parts or different types of parts, wherein properties within one part of the body structure are different from properties of other parts of the body structure. Further, heterogeneous body structures exhibit spatial variation in the aforementioned properties. In other words, a heterogeneous body structure is in particular anisotropic.

Biological tissues such as, for example, the brain or liver, are generally heterogeneous body structures that exhibit varying properties. In heterogenous body structures, an injected substance does not spread isotropically around the injection location. The target region at which the medical drug acts can therefore differ significantly from the injection point at which the medical drug is injected. This effect is caused by the heterogeneity and the different physical and physiological properties of the body structures in question. These differences can be present in a healthy body structure (e.g., anatomical, biological and/or physiological properties of the body structures) or can be generated or compounded by illnesses (e.g., from a tumor or bleeding). The vascularity of a tumor, for example, is very complex. The cells and vessels newly formed by the tumor can differ significantly in their properties from the cells and vessels of the healthy tissue. Blood vessels in a brain tumor for example, in particular in glial blastomata, do not have a functionally effective blood-brain barrier. For instance, the number of endothelial vesicles may be significantly increased in glial blastomata, and gaps may be found in the endothelial layer. In general, a significant change in the extra-cellular matrix of pathological vessels is seen in glial blastomata (the healthy brain includes cavities and folds which influence the distribution of fluid).

In the past, the aforementioned peculiarities of heterogeneous body structures have led to failures in the targeted local chemotherapy of glial blastomata in the brain. While laboratory experiments were significantly successful, this could not be repeated in humans. This was substantially due to the fact that the medical drug (in particular a chemotherapeutic agent in the case of glial blastomata) did not spread or did not sufficiently spread in the desired target region due to the heterogeneity of the brain, but was rather misdirected by the heterogeneity of the tissue. This can lead to problems in so-called CED pressure-driven drug dispensing (convection-enhanced delivery) for treating brain tumors.

SUMMARY OF THE INVENTION

An optimum injection region for infusing or injecting a medical drug is advantageously determined to achieve an optimum distribution of the drug in a desired target region. This is possible even when the desired target region is not directly accessible and only can be reached indirectly by injecting or infusing at another location. Relevant anisotropic parameters and characteristics include: the spatial distribution of hydraulic permeability; capillary permeability; hydraulic properties (fluid conductivity); parameters that describe a cell matrix, in particular a spatial change in extra-cellular space; vascularity of a tumor; and the tumor matrix properties, as outlined further below. The invention enables a best position (location) for the infusion or injection to be proposed, and the number of injection regions needed to reach and cover the desired target region.

Infusion and/or injection regions can be proposed without (if desired) the positioning a catheter and measuring an injection result to optimize the position of the injection regions, step-by-step, from the experience thus obtained from such positioning and measuring.

The method described herein can be used to determine at least one infusion and/or injection region. The infusion and/or injection region can be determined such that the injected medical drug acts in a desired target region, in particular at a desired concentration.

The method is based on using properties of the heterogeneous body structure to determine the at least one infusion and/or injection region. These properties can be properties that influence a spatial distribution of the medical drug, in particular a distribution of the concentration of the medical drug in the heterogeneous body structure (e.g., of the medical drug that is provided for injection in the at least one predetermined infusion and/or injection region of the heterogeneous body structure). "Heterogeneous" here means a spatial variation in the aforementioned properties or parameters. Accordingly, the properties are different at different locations of the body structure and are not homogeneously formed. The properties are in particular properties that influence the transport and/or loss of the drug.

The at least one infusion and/or injection region can be calculated as a function of the aforementioned properties of the heterogeneous body structure and the position of the at least one desired target region.

The aforementioned properties of the heterogeneous body structure that influence the spatial distribution of the medical drug in the heterogeneous body structure can be described by a "connectivity" of segments of the heterogeneous body structure that influences the transport of the medical drug. Connectivity can be a degree and/or measure of the connection between the segments, or also can be more simply described in binary, e.g., connected or not connected.

Connectivity describes the scope of transport of the drug from one segment to a connected, in particular adjacent, segment. The segments can be described as elements of a matrix. They also can have different sizes and/or shapes. The term "transport of the drug" here includes not only active transport processes, caused for example by flows and/or pressure gradients, but also, for example, passive transport processes, migration, diffusion, osmosis, perfusion, etc., e.g., any process that leads to a change in the spatial position of the drug.

The spatial distribution of the concentration of the drug is relevant to the medical effect of the drug. This can be influenced not only by the transport of the drug but also by loss of the drug. Loss of the drug can likewise be caused by drug transport processes if, for example, the drug is transported into regions outside the heterogeneous body structure under observation or into desirable regions that are not of interest for the medical effect. One substantial cause of loss of the drug is the permeability of parts of the heterogeneous body structure, e.g., of cell and/or vessel walls. A distribution of the concentration of the drug in the heterogeneous body structure and in particular a spread of the drug in the heterogeneous body structure can be determined by taking into account both the transport of the drug and the loss of the drug. In a preferred embodiment, a distinction is made between transport of the drug and loss of the drug. More specifically, transport of the drug transports the drug from one region (segment) to another region (segment) of the heterogeneous body structure under observation. Loss of the drug, on the other hand, reduces the drug in a region (segment) of the heterogeneous body structure under observation, without the loss leading to an increase in the amount or concentration of the drug in another region of the heterogeneous body structure under observation. Regions having a high capillary permeability and therefore a high risk of loss may not be regarded as a suitable infusion and/or injection region and, therefore, can be ruled out as infusion and/or injection regions.

The connectivity and/or transport of the drug and/or loss of the drug can be described by the hydraulic properties of the segments, in particular the capillary permeability and/or hydraulic conductivity (also known as "hydraulic permeability"). In the following, the capillary permeability is referred to as "permeability" for short. In order to describe the connectivity, reference is made to the arrangement of the elements, in particular to their proximity relationships with respect to each other. Values that describe the hydraulic properties of the segments can be examined as to their similarity and/or difference to determine the connectivity of the elements. If, for example, two adjacent segments have a high hydraulic conductivity, then a positive connectivity (high degree of connection) of the segments present, and a positive transport of the drug may be assumed. If, for example, adjacent segments have a low permeability, then these segments are very suitable for accumulating a high concentration of the drug, since the drug is not lost. The connectivity can be defined both for the hydraulic conductivity and for the capillary permeability. The connectivity relating to the capillary permeability substantially provides information about the scope of the loss. The greater the connectivity, the greater the loss will be. The connectivity relating to the hydraulic conductivity gives information corresponding to the spatial distribution of the fluid as well as indirect information concerning the concentration of the drug.

The drug, for example, can be physically transported from one region to another region by the weight and/or volume of the drug transported per unit of time and/or by describing the changes in concentration. Similarly, the loss of the drug can be physically described by the change in the volume and/or concentration of the drug in a region, in particular described per unit of time. The size, shape and/or rigidity of the segments and/or the number of proximity relationships (connections to adjacent segments) can be taken into account in order to determine the connectivity.

A probability calculation also can be performed in order to determine the connectivity. This can be based on the probability of a transport of the drug from one segment to another segment, wherein the theory of percolation, as is known in particular from geology, can be referenced.

In geology, percolation describes the migration of elemental, migratory particles of earth, so-called percolates, in the porous space of the ground. This theory can be applied to heterogeneous body structures in order to describe the migration or transport of the drug in the heterogeneous body structure, wherein percolation paths of the drug in the heterogeneous body structure can be calculated. In accordance with percolation theory, the bond percolation theory, for example, can be used to calculate the probability of a connection between a segment and an adjacent segment and, therefore, to determine percolation paths, wherein a directional degree of connection (connectivity) between one cell and an adjacent cell can be determined. This, for example, can be described using a vector field or tensor field, wherein each segment may be assigned a vector or tensor that describes the direction and size of the connection.

The medical drugs can be groups of molecules, e.g., highly specific toxins having specific bonding bodies (e.g., antigens or antibodies) that selectively couple onto glial blastomata, or fluids, liposomes, microspheres, compounds, viruses, viral vectors, cells, cellular components, genotype molecules, nanoparticles or other therapeutically effective substances that can be transported by fluids.

The calculated percolation paths, the determined connectivities between the segments or along a path, a probability plan that represents a probability for the distribution of the drug in each segment for predetermined injection regions, and proposed injection regions can be visualized and, for example, displayed on a monitor. The aforementioned visualizations are examples that can be displayed individually and/or in combination with other visualizations.

An expected ratio or relationship between the concentration and/or amount (in the at least one effective region) of the medical drug intended to be infused or injected and the injected concentration and/or amount can be determined. This enables the at least one injection region to be optimized. Preferably, an infusion and/or injection region is selected for which a maximum distribution of the drug in the desired target region results from a minimum injection amount. The aforementioned expected ratio (and/or relationship), the (absolute and/or relative) concentration and/or the (absolute and/or relative) amount of the medical drug provided for injection can be calculated at least as a function of at least one property of the injection conditions of the medical drug and/or at least one property of the medical drug.

The expected amount absorbed by the cells in the effective region and/or the amount absorbed can be calculated per unit of time. This may be calculated on the basis of the calculated concentration in the effective region and the absorption properties of the cells in the effective region, wherein in particular equations are referenced that describe the chemical equilibrium reactions between the drug and the cell.

A desired concentration in the target region, called the nominal effective concentration, can be predetermined. The nominal effective concentration represents a desired concentration in the target region of the medical drug provided for infusion and/or injection. On the basis of this, the method then can determine at least one desirable injection condition for injection and/or infusion of the medical drug. Injection conditions, for example, can include the amount of injected drug per unit of time, the concentration of the drug, the injection direction, the injection location, the trajectory of the injection device (e.g., catheter or needle), the injection pressure, the current flow of the injection, and/or the duration of the injection. The injection condition can be calculated on the basis of the determined position of the at least one infusion and/or injection region, such that the nominal injection conditions result in the desired nominal effective concentration in the target region.

The aforementioned properties of the heterogeneous body structure, which, as outlined above, can described by the permeability and hydraulic conductivity and connectivity, can also include or be represented by at least one of the following properties: properties that influence the transport of the medical drug, including drug structures in the heterogeneous body structure that can be transported by means of fluid. The transport of the medical drug also can be influenced by body fluid transport processes, e.g., flows, such as blood flows, along vessels.

Another example of such properties is the course and position of drains for the medical drug in the heterogeneous body structure. Examples include porous blood vessels such as those that occur in tumors and can lead to an increased, in particular undesirably increased drainage of the medical drug before it can reach the desired effective region.

Another example property is the absorption of the medical drug in the heterogeneous body structure, in particular by healthy cells, whereas absorption by pathological cells is in particular desired.

Yet another example of said properties is the diffusion of the medical drug that has reached the effective region and departed therefrom by diffusion. Other examples are provided below.
 a) The permeability of vessels that run in the heterogeneous body structure and are suitable for transporting the drug.
 b) The transport capacity of the vessels for the drug, which, for example, can be described by the flow velocity of the fluid in the vessels, the vessel diameter and the flow of the fluid in the vessel.
 c) The average dwelling time of the drug (which, for example, can be described by a concentration decay time in the vessel or in the cells).
 d) The hydraulic conductivity and/or drug conductivity from cells to adjacent cells or from vessels to adjacent vessels, in general from one segment to an adjacent segment.
 e) The percolation properties of the heterogeneous body structure.
 f) The provided position of the patient, and the consequent gravitational forces which can influence the percolation of the drug.

The aforementioned vessels and cells represent examples of parts of the heterogeneous body structure. Other examples are nerve cords and sulci. Where parts of the heterogeneous body structures are mentioned here, the parts can differ in their biological properties and in particular drug transport properties and/or drug loss properties. Tumor cells, for instance, have different drug transport properties to nerve cords. For determining the injection region, the heterogeneous body structure can be spatially divided into segments. The segments can be shaped such that they are each assigned to a part of the heterogeneous body structure that has a specific drug transport property. Data can therefore be predetermined for each segment of the heterogeneous body structure which describe the drug transport property of said segment and/or a loss of the drug in said segment. On the basis of these data, the spread of the drug and/or loss of the drug in the heterogeneous body structure, in particular in a spatial resolution, can then for example be calculated segment by segment.

The segments used for determining the spatial distribution of the connectivity and/or transport of the drug and/or loss of the drug can be smaller than the aforementioned (characteristic) parts of the heterogeneous body structure (e.g., vessels or cells, nerve cords). They can, however, also be larger, such that they can then be assigned an average measure of the connectivity and/or transport of the drug to adjacent segments and/or loss of the drug.

Examples of injection properties include:
 a) the amount of the medical drug provided for injection, e.g., integrated over the entire duration of the injection;
 b) the provided duration of the injection;
 c) the concentration of the medical drug provided for injection;
 d) the amount of the injection of the medical drug provided per unit of time; and
 e) the provided injection direction of the medical drug.
This also can be influenced by:
 a) the catheter bending;
 b) the provided flow velocity of the injection;
 c) the provided pressure of the injection;
 d) the provided shape of the injection apparatus for injection, in particular the size and/or shape of the exit opening in the injection apparatus for injection of the medical drug;
 f) the provided position of the injection apparatus in the heterogeneous body structure, in particular the position and/or orientation of the exit opening and/or the provided position and/or size of the volume occupied by the injection apparatus in the heterogeneous body structure;
 g) the position and/or size of the surface of the injection apparatus in the heterogeneous body structure; and
 h) the provided course of an insertion channel generated by the insertion of the injection apparatus, in particular the position, size and shape of the insertion channel.

Examples of drug properties that can be used to determine the optimum injection region include:
 a) the size and/or shape of the drug structures;
 b) the transportability (diffusion, flow, migration) of the drug structures in fluids, in particular in body fluid and/or injection fluid;
 c) the viscosity of the injection fluid; chemical and/or biological and/or physiological properties of the medical drug;
 d) the metabolic properties of the medical drug; and
 e) the penetration properties of the medical drug through barriers such as for example cell walls and/or the blood-brain barrier.

The invention further relates to planning the at least one infusion and/or injection region in order to be able to obtain an optimum injection region for an injection or infusion of the medical drug, wherein in said planning method, the previously described method for determining the at least one injection region is used. Also provided is a computer program which uses the aforementioned planning method, wherein when the computer program is loaded onto a computer, it causes the computer to perform the planning method.

A device also is provided that includes a calculating means (e.g., a data processing means) for performing the aforementioned method for determining the at least one infusion and/or injection region on the basis of the input of at least one desired target region. The aforementioned device can further include an injection instrument for injecting the medical drug. The device can alternatively or additionally include an analysis unit (monitoring unit), for example an x-ray apparatus, for determining the position of the injection region, if the injection instrument has been inserted into the heterogeneous body structure, so as to verify whether the desired injection region has been reached. The aforementioned device can further include diagnostic means that allow the properties of the heterogeneous body structure to be determined. The aforementioned data processing unit can further include a database that describes properties of parts of the heterogeneous body structure that influence the distribution of the drug in the heterogeneous body structure. For example, the database can include data concerning the permeability or rigidity of biologically different parts of the heterogeneous body structure such as, for example, tumor cells and tumor vessels and healthy cells and healthy vessels, as well as sulci and/or nerve cords, and the hydraulic conductivity of such parts.

Data describing the properties of the heterogeneous body structure that influence the spatial distribution of the medical drug in the heterogeneous body structure can be ascertained by diagnostic units. In particular, the so-called MR-DTI (diffusion tensor imaging) is preferably referenced. Other magnetic resonance methods and/or ultrasound methods and/or contrast methods also can be used to determine these properties. Examples include: magnetic resonance tomography (MRT); magnetic resonance angiography (MRA); functional MRT (fMRT); imaging the cellular blood flow (ASL); diffusion imaging (DWI); perfusion imaging (PWI); MR spectroscopy (MRS, SVS, CSI); and the diffusion tensor imaging (DTI) already mentioned. The latter in particular provides information concerning a spatial distribution and mobility of water molecules and provides an indication of the morphological integrity of the white and grey substance of the brain. It allows the movements of molecules to be differentiated in multiple spatial directions and, therefore, the tensor and/or vector matrices (which were mentioned above in connection with percolation theory and can describe the connectivity of segments). The diffusion of the drug, in particular the diffusion of molecules, is limited by different barriers, such as for example cell walls or membranous structures within the cells. Pathological changes, such as ischaemic, inflammatory, demyelinating changes in the tissue of the brain likewise also influence the diffusion behavior of molecules and in particular water molecules and drug molecules. Mobility is also significantly greater for example along the nerve fibers than perpendicular to the course of the fiber. The directionality (anisotropy) of the movement of molecules thus provides information about the course and the integrity of cerebral fiber connections. This also can be used to determine the connectivity of adjacent segments, in particular the direction of connectivity and the measure of connectivity as a function of the direction.

BRIEF DESCRIPTION OF THE DRAWINGS

The forgoing and other features of the invention are hereinafter discussed with reference to the drawing.

DETAILED DESCRIPTION

In the exemplary method described below for determining an infusion and/or injection region, and more particularly a segment in a heterogeneous body structure that is suitable for infusion, values concerning the (hydraulic) permeability of the segments can be combined with values concerning the hydraulic conductivity of the segments to obtain a percolation path from a possible injection segment to a desired target region, and in the present example the target segment. Other properties of the heterogeneous body structure can of course be adduced for determining the path and/or the suitable injection segment. It is also possible to only adduce either the hydraulic permeability or the hydraulic conductivity for the calculation.

In the example of FIG. 1, a segment matrix 10 includes 15 elements. The rows of the matrix are indicated by A, B and C, and the columns by 1, 2, 3, 4 and 5, so as to be able to refer to the individual segments in the following description.

The desired target segment is indicated by a circle and is located in segment A1. Multiple effective segments can of course also be desired and can be adjacent to one another or separated by at least one segment.

A barrier is schematically indicated by 20 and has the shape of a "U" lying on its side. The barrier 20 is intended to indicate that it is not possible to penetrate the region within the barrier in order to reach an injection segment with an injection instrument 30, or that an insertion path for the injection instrument 30 (e.g., catheter, syringe, needle) which penetrates the barrier 20 or the region 20 in general is undesirable for medical reasons. A region can be undesirable for the insertion path, for example, on the grounds of an increased, undesirable so-called backflow of the drug along the inserted injection instrument and, therefore, an undesirable loss of the drug. A region also may be undesirable on the grounds that tracking the course of the insertion path via imaging diagnostic apparatus (e.g., x-ray) can be difficult, or on the grounds of possible injury to body structures.

Due to the barrier 20, it is therefore assumed that in the situation shown in FIG. 1, only the segments A5, B5 and C5 are possible injection segments. However, the desired target segment is A1, which is several segments away from the possible injection segments.

The method described herein can determine whether one of the segments A5, B5 or C5 is suitable for an injection so as to achieve an affect in the target segment A1. If not, an injection can be abandoned. If so, the method can determine which of the available segments for the injection is the most suitable.

Segments that are suitable for an infusion and/or injection are segments having a low loss of the drug, where a concentration of the drug can therefore be accumulated that is then further dispersed by pressure-driven spreading and/or diffusion. Segments having a high loss of the drug can be interpreted as drains for the concentration of the drug. A loss of the drug can be caused by transport of the drug (e.g., diffusion, passive transport, pressure-driven transport, ion transport, transport due to a membrane potential, osmosis, active transport) for example through a membrane of a cell. This means that a low permeability of the membrane for drug transport processes promotes the accumulation of a high concentration of the drug.

The permeability of vessels, for example, can be measured by perfusion measurements using magnetic resonance, ultrasound or CT techniques and, therefore, can be provided to the method as information for further calculation. Segments for which a low permeability has been identified are therefore favorable, since only a small loss of the drug occurs in such segments. Segments exhibiting a high permeability represent a drain for the drug, since the drug lost via these segments. Examples of such cells are tumor blood vessels in the brain having a highly permeable vessel wall.

Figure 1A:
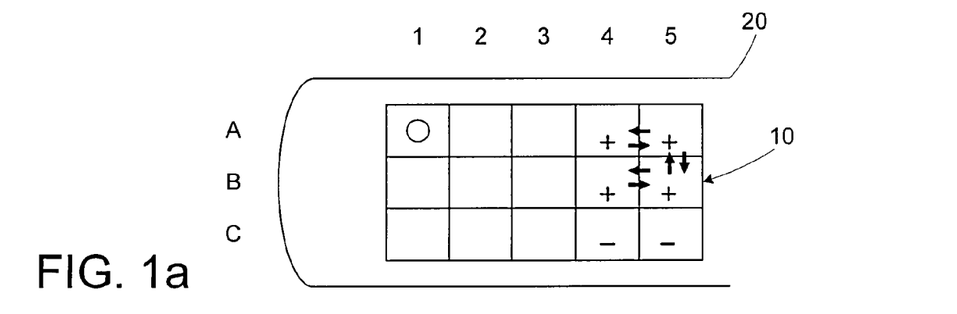
FIG. 1a shows an exemplary matrix of segments in accordance with the invention, wherein the segments are assigned permeability values.

Segments exhibiting a low loss of the drug (low permeability) therefore have advantageous injection properties and are indicated by a "+" in FIG. 1a. Segments exhibiting a high loss of the drug (high permeability) in which a high loss of the drug is to be feared, are indicated by a "−" in FIG. 1a. Further, simple arrows in FIG. 1a indicate the possible spread of the concentration of the drug. An average dwell time of the concentration of the drug in a segment, for example, can be a measure of the loss of the drug.

It can be seen from FIG. 1a that, of the segments A5, B5 and C5 available for the injection, segments A5 and B5 would be suitable. Segment A5 seems particularly suitable, since if injected into A5, the drug can spread into the adjacent segments A4 and B4 and B5 by slowly diffusing, without the drug being lost due to high permeability. It is therefore possible to accumulate a high concentration of the drug in the cells A4, A5, B4 and B5, since no loss means higher concentrations. It can, however, transpire that a high connectivity and therefore a large spatial distribution leads to a low concentration. This depends on the type of transport. If the transport process is diffusion-driven, this can lead to lower concentrations. If it is pressure-driven, a high connectivity does not normally cause a lower concentration.

The segments shown in FIG. 1 in particular are each a mixture of blood cells, cells and matrix tissue (e.g., the space between the cells). This can be caused by the spatial resolution of the mapping techniques and therefore by the data material. At a higher resolution, individual segments even can be assigned to individual blood cells. The fluid will migrate through the tissue matrix, and the capillary permeability relates in particular to the vessels or capillaries. A segment exhibiting a high/low permeability therefore means that there is a risk of high/low loss in said segment. A segment exhibiting a high/low permeability means a high/low risk of fluid loss.

On the other hand, the effect of hydraulic conductivity is that the transport can be increased or reduced, independent of the vessels at said location, because the matrix is heterogeneous. Segments exhibiting a high loss of drug (a high permeability) are characterized by a "−" in FIG. 1a. The segment 5C is therefore not suitable for injecting the drug, since the drug would quickly depart from the cell and it would therefore not be possible to accumulate a concentration of the drug. As for the remaining cells A1 to A3, B1 to B3 and C1 to C3, it is assumed that they exhibit an average loss of the drug which is unfavorable for spreading the drug by means of diffusion from the cells A4, A5, B4 and B5 to A1, or that information about the loss of the drug is not available for these regions.

In addition to the mechanism of spreading the drug by diffusion, there also are other transport mechanisms such as for example spreading by means of hydraulic conductivity. This is discussed further below in connection with FIG. 1b and can be used to transport the drug to the desired effective segment.

Figure 1B:
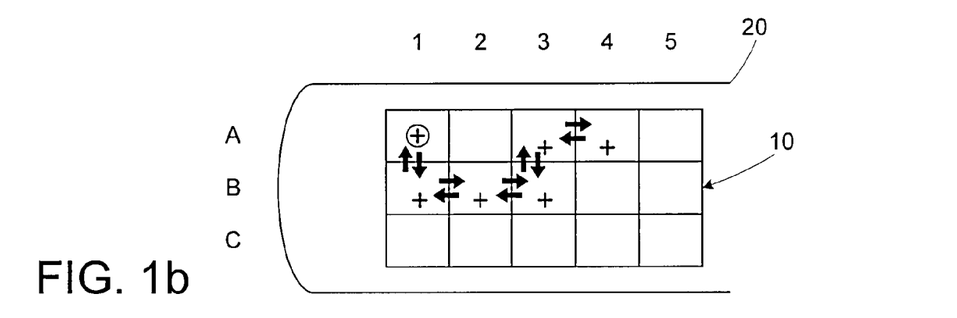
FIG. 1b shows an exemplary matrix comprising segments in accordance with the invention, wherein the segments are assigned a conductivity value.

FIG. 1b shows a matrix that relates to hydraulic conductivity. A high hydraulic conductivity present in the segments is characterized by a "+". A vessel or nerve cord can for example run along A4, A3, B3, B2, B1 and A1.

A higher hydraulic conductivity, which is favorable for the transport of the drug, is present along healthy vessels or nerve cells. In FIG. 1b, the possible transport of the drug by hydraulic conductivity is indicated by thick arrows. In particular, a connectivity is present between the segments A3 and A4, such that a distribution of the drug in segment A4 to A1 is possible via the segments A4, A3, B3, B2, B1. As previously outlined, the connection between the segment B3 and B4 is small, due to the properties of vessel walls transverse to the direction of transport, such that a spread of the drug from the segment B4 to B3 cannot be assumed.

The arrows shown in FIG. 1a and 1b can be assigned values or probabilities that describe the degree and direction of connectivity of adjacent segments. The values in FIGS. 1a and 1b can be combined with each other, in order to determine a transport path (also called percolation path herein) of the drug from an injection segment to an effective segment. The effectiveness of the transport of the drug can be calculated on the basis of said values or probabilities, such that the amount of the drug to be injected can be calculated from the desired concentration of the drug in the target segment.

Figure 1C:
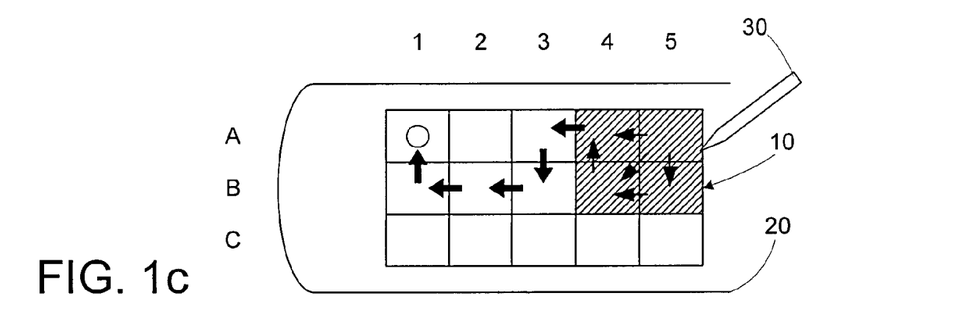
FIG. 1c shows an exemplary percolation path from an injection region to an effective region in accordance with the invention.

FIG. 1c shows a matrix that describes the spread of the drug along the segments. It is also called a percolation matrix. The thin arrows indicate the spread of the drug in the shaded segments A4, A5, B4 and B5. A high concentration of the drug accumulates in these segments, starting from the segment A5. The diffusion from segment A5 into the adjacent segments A4, B4 and B5 is characterized by a thin arrow. The drug is transported away from the segment A4 by hydraulic conductivity, along the segments A4, A3, B3, B2, B1 and A1. Transporting the drug away from the segment A4 results in a decrease in the drug, which can be compensated for by diffusion from the segment A5 or also from the segment B4, as indicated by small arrows. The desired effective segment can therefore be reached by injecting the drug in the segment A5.

Figure 1D:
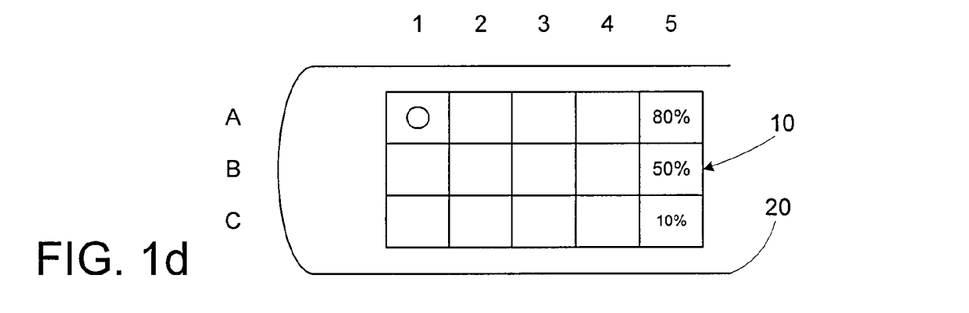
FIG. 1d shows a probability matrix in accordance with the invention.

FIG. 1d shows a probability matrix in which a probability that a desired concentration of the drug can be achieved in the target segment A1 by injection in each segment is indicated on the basis of the data concerning the permeability and hydraulic conductivity for the possible injection segments A5, B5 and C5. Ancillary conditions such as drug properties and injection properties, such as for example the maximum amount of the drug that can be injected, in particular also per unit of time, can of course also be taken into account.

Using the method described herein, it is possible to determine infusion and/or injection regions that differ with regard to the target regions that can be reached. This is in particular advantageous when an injection in the target region is not possible or when a direct injection in the target region from an incorrect direction would lead to a high loss of the drug. In particular, it is also possible to determine whether a plurality of target segments can be reached by injection into one or more injection regions, so as to reach as many as possible or all the target cells (e.g., tumor cells) with the drug.

Conventionally, multiple infusion regions are provided, for example four, which lie around the desired target region. If, however, the anisotropy of the body structure is not taken into account, some or even all of the injection regions may prove to be unsuitable, such that the desired target region is not reached by the drug, or a desired concentration of the drug cannot be achieved in the target region. This can be prevented by the method described herein. Lastly, it is also possible to plan which regions are to be reached. It is for example possible to reach only a region within the tumor or to reach regions outside the tumor, in order to destroy nascent metastases of the tumor that cannot yet be fully detected by image diagnosis.

Figure 2:
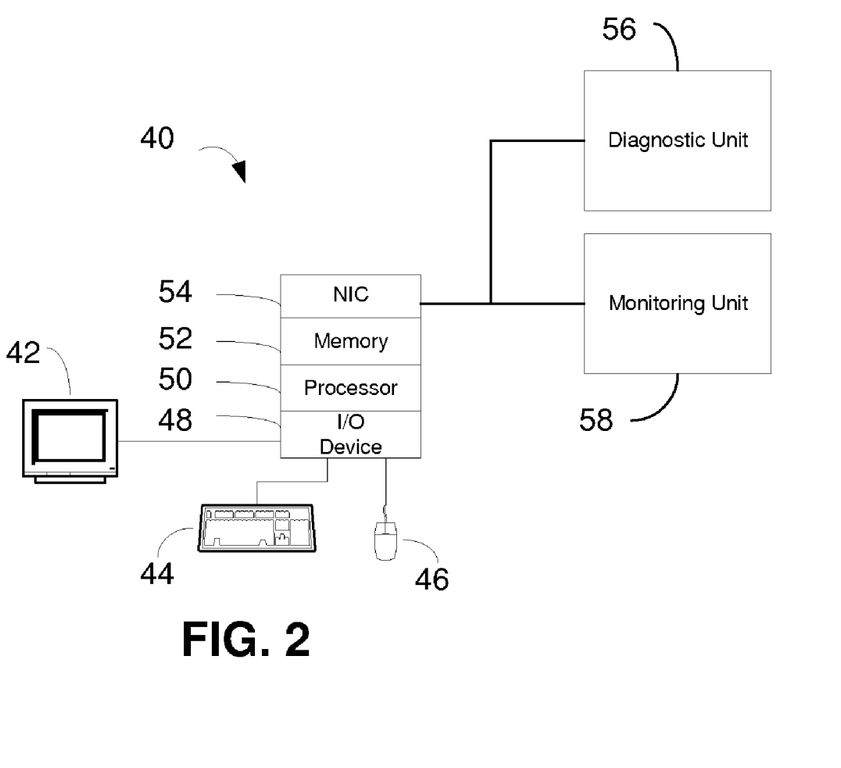
FIG. 2 is a block diagram of an exemplary computer system that may be used to carry out one or more of the methods described herein.

Moving now to FIG. 2 there is shown a block diagram of an exemplary computer 40 that may be used to implement one or more of the methods described herein. The computer 40 may include a display 42 for viewing system information, and a keyboard 44 and pointing device 46 for data entry, screen navigation, etc. A computer mouse or other device that points to or otherwise identifies a location, action, etc., e.g., by a point and click method or some other method, are examples of a pointing device 46. Alternatively, a touch screen (not shown) may be used in place of the keyboard 44 and pointing device 46. The display 42, keyboard 44 and mouse 46 communicate with a processor via an input/output device 48, such as a video card and/or serial port (e.g., a USB port or the like).

A processor 50, such as an AMD Athlon 64® processor or an Intel Pentium IV® processor, combined with a memory 52 execute programs to perform various functions, such as data entry, numerical calculations, screen display, system setup, etc. The memory 52 may comprise several devices, including volatile and non-volatile memory components. Accordingly, the memory 52 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 50 and the memory 52 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 54 allows the computer 40 to communicate with other devices.

A diagnostic unit 56 for obtaining data concerning properties of the body structure is communicatively coupled to the processor 50 via the NIC 54. Similarly, a monitoring unit 58, such as an x-ray imaging device, also is communicatively coupled to the processor via the NIC 54.

A person having ordinary skill in the art of computer programming and applications of programming for computer systems would be able in view of the description provided herein to program a computer system 40 to operate and to carry out the functions described herein. Accordingly, details as to the specific programming code have been omitted for the sake of brevity. Also, while software in the memory 52 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer implemented method for determining at least one infusion and/or injection region for infusing and/or injecting a medical drug into a heterogeneous body structure in order to achieve a distribution of the medical drug in a desired target region of the heterogeneous body structure, comprising:
    providing at least one property of the heterogeneous body structure that influences a spatial distribution of the medical drug in the heterogeneous body structure;
    determining, using a processor, the at least one infusion and/or injection region from which the medical drug is to be transported through the heterogeneous body structure to the at least one target region as a function of the at least one property of the heterogeneous body structure and a position of the desired target region,
    wherein the heterogeneous body structure is spatially divided into a plurality of segments and the probability of transport of the medical drug from one of said plurality of segments to another one of said plurality of segments is determined, said probability of transport determined based on percolation theory that includes calculating a probability of connection between adjacent segments to determine a percolation path; and
    outputting the at least one infusion and/or injection region via an output device.

2. The method according to claim 1, wherein the heterogeneous body structure comprises biological tissue.

3. The method according to claim 1, wherein providing the at least one property of the heterogeneous body structure includes providing a drug transport property and/or drug loss property that spatially varies in the heterogeneous body structure.

4. The method according to claim 1, wherein providing the at least one property of the heterogeneous body structure includes determining a connectivity of the plurality of segments of the heterogeneous body structure that influence the transport of the drug based on the at least one property, and determining the at least one infusion and/or injection region includes basing the determination on the connectivity of the plurality of segments.

5. The method according to claim 4, wherein determining the connectivity of the plurality of segments of the heterogeneous body structure includes basing said connectivity on permeability and/or hydraulic conductivity properties of the plurality of segments.

6. The method according to claim 4, wherein determining the connectivity of the plurality of segments of the heterogeneous body structure includes basing the determination on an arrangement, size and/or shape of the plurality of segments and/or by a number of adjacent segments.

7. The method according to claim 4, further comprising determining a loss of the drug in segments of the heterogeneous body structure based on the at least one property of the heterogeneous body structure, and wherein determining the at least one infusion and/or injection region includes basing the determination on the loss of the drug in the segments.

8. The method according to claim 4, wherein determining the loss of the drug includes basing said loss on permeability and/or hydraulic conductivity properties of the plurality of segments.

9. The method according to claim 4, further comprising calculating a probability for the connectivity and/or loss of the drug for the plurality of segments, and using the calculated probability to determine segments of the plurality of segments that are suitable for an injection so as to achieve a predetermined distribution of the drug in the target region.

10. The method according to claim 1, further comprising visually displaying at least one of:
a) one or more possible drug transport paths from the at least one determined infusion and/or injection region to the target region;
b) a probability for each segment of a plurality of segments of the heterogeneous body structure that a distribution of the medical drug in the target region will be achieved when infusing and/or injecting the drug into the corresponding segment of the plurality of segments;
c) connectivity of adjacent segments;
d) loss of the drug in segments; or
e) possible segments of the heterogeneous body structure suitable for the injection.

11. The method according to claim 1, further comprising calculating an expected ratio between a concentration and/or amount of the medical drug in the target region and an injected concentration and/or amount of the medical drug as a function of the at least one property of the heterogeneous body structure and as a function of the determined infusion and/or injection region.

12. The method according to claim 11, wherein calculating the expected ratio between the concentration and/or amount of the medical drug includes calculating the expected ratio as a function of at least one drug property and/or at least one injection property.

13. The method according to claim 1, further comprising calculating an expected amount of the medical drug absorbed by cells in the target region as a whole or per unit of time based on a calculated concentration for the target region drug absorption properties of cells in the target region.

14. The method according to claim 1, wherein the properties of the heterogeneous body structure include at least one of:
properties that influence the transport of the medical drug and/or drug molecules that are transportable by fluid in the heterogeneous body structure based on body fluid transport processes;
a course and position of drains for the medical drug in the heterogeneous body structure;
properties that influence the absorption of the medical drug in the heterogeneous body structure;
properties that influence the diffusion of the medical drug in the target region;
hydraulic conductivity of parts of the heterogeneous body structure that run in the heterogeneous body structure and are suitable for transporting the drug to adjacent parts of the heterogeneous body structure;
transport capacity of parts of the heterogeneous body structure for the drug;
a loss of the drug through parts of the heterogeneous body structure that differ in biological properties;
percolation properties of the heterogeneous body structure; or
a provided position of the patient.

15. The method according to claim 14, wherein the hydraulic conductivity of parts of the heterogeneous body structure include vessels, nerve cords, sulci, hollow spaces and/or cells.

16. The method according to claim 14, wherein the transport capacity of parts of the heterogeneous body structure for the drug includes the transport capacity of vessels, nerve cords, sulci and/or hollow spaces.

17. The method according to claim 14, wherein the loss of the drug through parts of the heterogeneous body structure that differ in biological properties include loss through cells, vessels, nerve cords, sulci and/or hollow spaces.

18. The method according to claim 1, further comprising planning the infusion and/or injection based on the determined at least one infusion and/or injection region.

19. The method according to claim 1, further comprising determining percolation paths of the medical drug in the heterogeneous body structure.

20. The method according to claim 1, wherein calculating a probability of connection between adjacent segments to determine a percolation path includes determining a directional degree of connectivity between one cell and an adjacent cell.

* * * * *